United States Patent
Benicewicz et al.

(10) Patent No.: US 7,332,552 B2
(45) Date of Patent: Feb. 19, 2008

(54) LOW ODOR CHAIN TRANSFER AGENTS FOR CONTROLLED RADICAL POLYMERIZATION

(75) Inventors: Brian Benicewicz, Loudonville, NY (US); Chunzhao Li, Hightstown, NJ (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 10/583,681

(22) PCT Filed: May 27, 2004

(86) PCT No.: PCT/US2004/016718

§ 371 (c)(1),
(2), (4) Date: Dec. 18, 2006

(87) PCT Pub. No.: WO2004/108770

PCT Pub. Date: Dec. 16, 2004

(65) Prior Publication Data

US 2007/0088140 A1    Apr. 19, 2007

Related U.S. Application Data

(60) Provisional application No. 60/474,538, filed on May 30, 2003.

(51) Int. Cl.
*C08F 2/38* (2006.01)
*C07C 327/16* (2006.01)

(52) U.S. Cl. ............ 526/220; 526/222; 558/230; 558/235; 558/236

(58) Field of Classification Search ......... 526/220, 526/222; 558/230, 238, 243, 235, 236
See application file for complete search history.

(56) References Cited

U.S. PATENT DOCUMENTS 3,646,094 A  2/1972 Brooks et al.
6,153,705 A 11/2000 Corpart et al.

FOREIGN PATENT DOCUMENTS

WO   98/01478   1/1998

OTHER PUBLICATIONS

Chiefari et al, "Living Free-Radical Polymerization by Reversible Addition-Fragmentation Chain Transfer: The RAFT Process", CSIRO Molecular Science, Bag 10, Clayton South, Clayton, Victoria 3169, Australia, Received Mar. 27, 1998, Revised Manuscript Received Jun. 10, 1998 (four pages).*

Mayadunne et al, "Living Radical Polymerization with Reversible Addition-Fragmentation Chain Transfer (RAFT Polymerization) Using Dithiocarbamates as Chain Transfer Agents", *Macromolecules* 1999, 32, 6977-6980.*

Thang et al., "A Novel Synthesis of Functional Dithioesters, Dithiocarbamates, Xanthates and Trithiocarbonates," *Tetrahedron Letters* 40, pp. 2435-2438 (1999).

Sudalai et al., "Phosphorus Pentasulfied: A Mild and Versatile Catalyst/Reagent for the Preparation of Dithiocarboxylic Esters," *Organic Letters*, vol. 2(20), pp. 3213-3216 (2000).

Kanagasabapathy et al., "Montmorillonite K 10-catalyzed regioselective addition of thiols and thiobenzoic acids onto olefins: an efficient synthesis of dithiocarboxylic esters," *Tetrahedron Letters* 42, pp. 3791-3794 (2001).

* cited by examiner

*Primary Examiner*—Fred Teskin
(74) *Attorney, Agent, or Firm*—Heslin Rothenberg Farley & Mesiti P.C.

(57) ABSTRACT

The present invention relates to low odor α-cyano-dithiocarboxylic ester compounds of formula I for use as chain transfer agents in free radical polymerizations, and polymerization processes employing them:

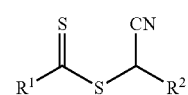

wherein
$R^1$ is selected from alkyl, substituted alkyl, heteroaryl, substituted heteroaryl, alkylaryl, substituted alkylaryl, aryl, substituted aryl, alkoxy, aryloxy, thioalkyl, thioaryl, substituted thioalkyl, substituted thioaryl, secondary amino and tertiary amino;
$R^2$ is selected from alkyl, aryl, substituted aryl, heteroaryl, substituted heteroaryl, and $COOR^3$; and
$R^3$ is alkyl.

14 Claims, No Drawings

LOW ODOR CHAIN TRANSFER AGENTS FOR CONTROLLED RADICAL POLYMERIZATION

CROSS REFERENCE TO RELATED APPLICATIONS

This application is a 35 U.S.C. § 371 U.S. national stage filing from PCT Application Ser. No. PCT/US04/016718 having international filing date of May 27, 2004, published in English under WO 2004/108770 A1 on Dec. 16, 2004, which claims priority from U.S. Provisional Application Ser. No. 60/474,538, filed May 30, 2003.

FIELD OF THE INVENTION

The invention relates to α-cyano-dithiocarboxylic ester compounds for use as chain transfer agents in free radical polymerizations.

BACKGROUND OF THE INVENTION

A living polymerization process is one that can produce polymers of predetermined molecular weight and a narrow molecular weight distribution containing one or more monomer sequences, the length and composition of which are controlled by stoichiometry of the polymerization reaction and degree of conversion. Accordingly, homopolymers, random co-polymers and block co-polymers, as well as polymers of more complex architectures, including branched homopolymers and co-polymers of low polydispersity may be produced with a high degree of control. Characteristics of a living polymerization process include:

"1. Polymerization proceeds until all of the monomer has been consumed. Further addition of monomer results in continued polymerization.
2. The number average molecular weight (or the number average degree of polymerization) is a linear function of conversion.
3. The number of polymer molecules (and active centers) is a constant which is sensibly independent of conversion.
4. The molecular weight can be controlled by the stoichiometry of the reaction.
5. Narrow molecular weight distribution polymers are produced.
6. Block copolymers can be prepared by sequential monomer addition.
7. Chain end-functionalized polymers can be prepared in quantitative yield."

(Quirk and Lee (*Polymer International* 27, 359 (1992))

Commercial processes for the production of living polymers typically employ anionic initiators. In contrast, free radical polymerization processes possessing living characteristics have only recently been developed. (See, for example, published International Application WO 98/01478.). Such free radical processes use addition-fragmentation chain transfer agents to facilitate reversible chain transfer so that the polymerization has living characteristics. This type of polymerization has been termed reversible addition-fragmentation-termination (RAFT) polymerization.

WO 98/01468 discloses a class of dithiocarboxylic esters for use as chain transfer agents in free radical living polymerization processes. These chain transfer agents have the structure of formula C or D:

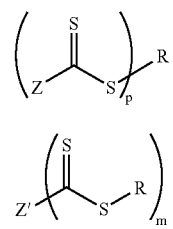

C

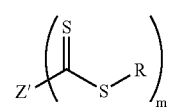

D wherein

Z is selected from the group consisting of hydrogen, chlorine, optionally substituted alkyl, optionally substituted aryl, optionally substituted heterocyclyl, optionally substituted alkylthio, optionally substituted alkoxycarbonyl, optionally substituted aryloxycarbonyl (—COOR"), carboxy (—COOH), optionally substituted acyloxy (—O$_2$CR"), optionally substituted carbamoyl (—CONR"2), cyano (—CN), dialkyl- or diaryl-phosphonato (—P(=O)OR"$_2$), dialkyl- or diaryl-phosphinato (—P(=O)R"$_2$), and a polymer chain formed by any mechanism;

Z' is a m-valent moiety derived from a member of the group consisting of optionally substituted alkyl, optionally substituted aryl and a polymer chain;

where the connecting moieties are selected from the group that consists of aliphatic carbon, aromatic carbon, and sulfur;

R is selected from the group consisting of optionally substituted alkyl, an optionally substituted saturated, unsaturated or aromatic carbocyclic or heterocyclic ring; optionally substituted alkylthio; optionally substituted alkoxy; optionally substituted dialkylamino; an organometallic species; and a polymer chain prepared by any polymerization mechanism; in compounds C and D, R. is a free-radical leaving group that initiates free radical polymerization;

R" is selected from the group consisting of optionally substituted C$_1$-C$_{18}$ alkyl, C$_2$-C$_{18}$ alkenyl, aryl, heterocyclyl, aralkyl, alkaryl wherein the substituents are independently selected from the group that consists of epoxy, hydroxy, alkoxy, acyl, acyloxy, carboxy (and salts), sulfonic acid (and salts), alkoxy- or aryloxycarbonyl, isocyanato, cyano, silyl, halo, and dialkylamino;

p is 1 or an integer greater than 1; when p is greater than or equal to 2, then R=R'; and m is an integer greater than or equal to 2.

Although these compounds function effectively as chain transfer agents, they share one major disadvantage with the entire class of sulfur-based compounds, a characteristic disagreeable odor. While this is an inconvenience during synthesis and/or production of the polymer in the laboratory, toxicity of the compounds and/or difficulty in handling large quantities of compounds having such a powerful and offensive odor may preclude use in industrial scale processes. In addition, residual odor in the product may be sufficiently objectionable to bar use in its intended application, or at least limit the amount that can be tolerated in a polymer for commercial use. It can be seen, then, that there is a continuing need for chain transfer agents lacking the characteristically offensive sulfur odor.

SUMMARY OF THE INVENTION

It has been unexpectedly discovered that dithiocarboxylic esters having a cyano group attached to a carbon atom adjacent to the 'thio' sulfur atom lack any disagreeable odor. The compounds have the structure of formula I.

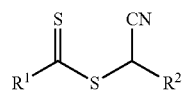

I wherein
- $R^1$ is selected from alkyl, substituted alkyl, heteroaryl, substituted heteroaryl, alkylaryl, substituted alkylaryl, aryl, substituted aryl, alkoxy, aryloxy, thioalkyl, thioaryl, substituted thioalkyl, substituted thioaryl, secondary amino and tertiary amino;
- $R^2$ is selected from alkyl, aryl, substituted aryl, heteroaryl, substituted heteroaryl, and $COOR^3$ and
- $R^3$ is alkyl.

At the same time, these compounds retain the ability of dithiocarboxylic esters to effectively function as chain transfer agents, especially in living polymerization processes.

Accordingly, in one aspect the present invention relates to a living polymerization process including combining at least one chain transfer agent of formula I, monomer(s) and a free radical initiator, and generating free radicals, whereby a polymer comprising repeating units derived from the monomer(s) is formed.

In another aspect, the invention relates to compounds of formula II

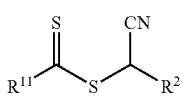

II wherein
- $R^{11}$ is selected from alkyl, substituted alkyl, heteroaryl, substituted heteroaryl, alkylaryl, substituted alkylaryl, aryl, substituted aryl aryloxy, thioalkyl, thioaryl, substituted thioalkyl, and substituted thioaryl; and
- $R^2$ is selected from alkyl, aryl, substituted aryl, heteroaryl, substituted heteroaryl, and $COOR^3$ and
- $R^3$ is alkyl.

The genus encompassed by formula II is a subset of that of formula I, and shares the same attributes, that is, lack of a disagreeable odor and ability to function as chain transfer agent in a free radical polymerization. U.S. Pat. No. 3,646,094 discloses α-cyanobenzyl xanthates and dithiocarbamates which fall outside the genus of formula II, for use as pesticides, and, to applicants' knowledge, compounds of formula II have not been disclosed in the literature.

DETAILED DESCRIPTION OF THE INVENTION

The present invention relates to improved dithiocarboxylic ester chain transfer agents that lack the characteristic offensive odor of sulfur compounds, while possessing the ability to provide good control over molecular weight, molecular weight distribution (polydispersity) and polymer architecture when used in a free radical polymerization process.

The chain transfer agents of the present invention have the structure of formula I:

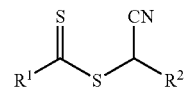

I wherein
- $R^1$ is selected from alkyl, substituted alkyl, heteroaryl, substituted heteroaryl, alkylaryl, substituted alkylaryl, aryl, substituted aryl, alkoxy, aryloxy, thioalkyl, thioaryl, substituted thioalkyl, substituted thioaryl, secondary amino and tertiary amino;
- $R^2$ is selected from allyl, aryl, substituted aryl, heteroaryl, substituted heteroaryl, and $COOR^3$ and
- $R^3$ is alkyl.

In a preferred embodiment, $R^2$ is aryl, and, more preferably, phenyl. Preferred substituents for use as $R^1$ are aryl, substituted aryl, alkoxy, and secondary or tertiary amino. (Where $R^1$ is alkoxy, the compounds are referred to as xanthate esters, and where $R^1$ is secondary tertiary amino, the compounds are referred to dithiocarbamate esters.) Exemplary compounds of formula I include:

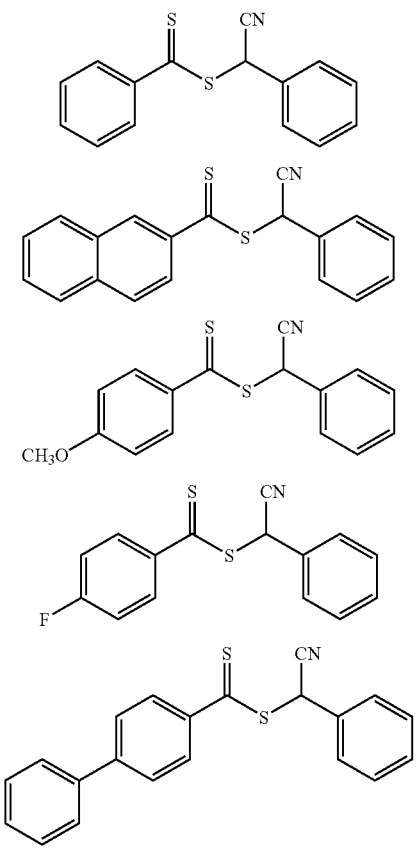

-continued

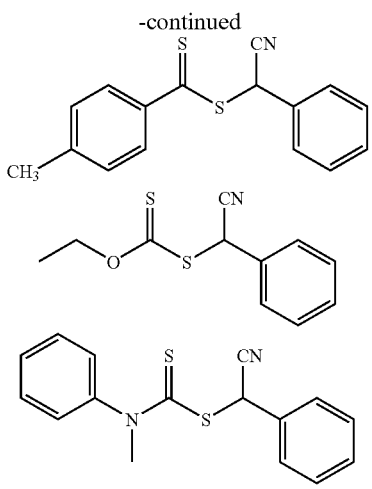

Synthesis of compounds of formula I is illustrated in the Examples section. In addition, synthesis of 'thiocarbonyl thio' compounds which do not contain the α-cyano substitution of the chain transfer agents of the present invention is described in WO 98/01478, and another process for preparing these dithiocarboxylic esters is described in U.S. Pat. No. 6,458,968.

A polymerization process according to the present invention employs one or more compounds of formula I as chain transfer agent(s). While such a polymerization process may be a RAFT process and have the characteristics of a living polymerization, the compounds of formula I may be useful in processes that do not meet the requirements for a living polymerization. Polymers having low polydispersity may be produced using the process of the present invention. In the context of the present invention, low polydispersity polymers are those with polydispersities that are significantly less than those produced by conventional free radical polymerization. In conventional free radical polymerization, polydispersities (the polydispersity is defined as the ratio of the weight average and number average molecular weights—Mw/Mn) of the polymers formed are typically in the range 1.6-2.0 for low conversions (<10%) and are substantially greater than this for higher conversions. Polydispersities obtained with the present invention are usually less than 1.5, often less than 1.3 and, with appropriate choice of the chain transfer agent and the reaction conditions, may be less than 1.1. The low polydispersity can be maintained at high conversions.

A polymerization according to the present invention includes combining at least one monomer susceptible to free radical polymerization, a free radical initiator and a chain transfer agent of formula I, and generating free radicals, whereby a polymer comprising repeating unit derived from the monomer(s) is formed. Free radicals suitable for initiating polymerization may be generated by any suitable method, including scission of a suitable compound(s) by redox, thermally induced homolysis (thermal initiators such as peroxides, peroxyesters, or azo compounds), or photolysis by exposure to light or to high energy radiation such as electron beam, X- or gamma-radiation. Radicals may also be generated spontaneously from monomer (e.g., styrene). The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture.

Thermal initiators are chosen to have an appropriate half-life at the temperature of polymerization. These initiators can include one or more of the following compounds: 2,2'-azobis(isobutyronitrile), 2,2'-azobis(2-cyano-2-butane), dimethyl-2,2'-azobis-dimethyl isobutyrate, 4,4'-azobis(4-cyanopentanoic acid), 1,1'-azobis (cyclohexanecarbonitrile), 2-(t-butylazo)-2-cyanopropane, 2,2'-azobis[2-methyl-N-(1,1)-bis(hydoxymethyl)-2-hydroxyethyl]propionamide, 2,2'-azobis[2-methyl-N-hydroxyethyl)]-propionamide, 2,2'-azobis(N,N'dimethyleneisobutyramidine)dihydrochloride, 2,2'-azobis(2-amidinopropane) dihydrochloride, 2,2'-azobis(N,N'-dimethylene isobutyramine), 2,2'-azobis(2-methyl-N-[1,1-bis hydroxy methyl)-2-hydroxyethyl]propionamide), 2,2'-azobis(2-methyl-N-[1,1-bis-(hydroxymethyl)ethyl] propionamide), 2,2'-azobis[2-methyl-N-(2-hydroxyethyl) propionamide], 2,2'-azobis (isobutyramide)dihydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, dicumyl hyponitrite.

Photochemical initiator systems are chosen to have an appropriate quantum yield for radical production under the conditions of the polymerization. Examples include benzoin derivatives, benzophenone, acyl phosphine oxides, and photoredox systems. Redox initiator systems are chosen to have an appropriate rate of radical production under the conditions of the polymerization; these initiating systems can include combinations of the following oxidants and reductants:

oxidants: potassium peroxydisulfate, hydrogen peroxide, t-butyl hydroperoxide; and reductants: iron (II), titanium (III), potassium thiosulfite, potassium bisulfite.

Other suitable initiating systems are described in recent texts. See, for example, Moad and Solomon, "The Chemistry of Free Radical Polymerization", pp 53-95 (1995).

Monomers that are susceptible to free radical polymerization include vinyl monomers, including acrylic and methacrylic acid, α-olefins and diolefins, maleic anhydride, maleimides and fumarates. Specific examples include: methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methyl styrene. methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from chloromethylstyrene (all isomers); fluorinated styrenes (all isomers), glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylamino-ethyl methacrylate, triethyleneglycol methacrylate, itaconic anhydride. itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-t-butyl methacrylamide, N-n-butyl methacrylamide, N-methylol methacrylamide, N-ethylol methacrylamide, N-t-butyl acrylamide. N-n-butyl acrylamide, N-methylol acrylamide, N-ethylol acrylamide, vinyl benzoic acid (all isomers), diethylaminostyrene (all isomers), alpha-methylvinyl benzoic acid (all isomers), diethylamine alpha-methyl styrene (all isomers). p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene, propylene.

Considerations in choosing a chain transfer agent (CTA) for a particular polymer include chain transfer constant and solubility parameters. High chain transfer constant is typically correlated with low polydispersity. In addition, a higher chain transfer constant allows greater flexibility in the choice of reaction conditions, as use of a feed addition process is typically advantageous for obtaining low polydispersity with reagents having low chain transfer constants. It is also possible to produce polymers with broad, yet controlled, polydispersity or multimodal molecular weight distribution by controlled addition of the CTA over the course of the polymerization process.

Solubility parameter is particularly significant for heterogeneous polymerization. For example, in aqueous emulsion polymerization, the CTA should preferably partition in favor of the organic (monomer) phase and yet have sufficient aqueous solubility that it is able to distribute between the monomer droplet phase and the polymerization locus.

Polymerizations conditions are typically chosen such that the number of chains formed from initiator-derived radicals is minimized to an extent consistent with obtaining an acceptable rate of polymerization. Termination of polymerization by radical-radical reaction will lead to chains which contain no active group and therefore cannot be reactivated. The rate of radical-radical termination is proportional to the square of the radical concentration. Furthermore, in the synthesis of block, star or branched polymers, chains formed from initiator-derived radicals will constitute a linear homopolymer impurity in the final product. These reaction conditions, therefore, require careful choice of the initiator concentration and, where appropriate, the rate of the initiator feed. It is also desirable to choose other components of the polymerization medium (for example, the solvents, surfactants, additives, and initiator) such that they have a low transfer constant towards the propagating radical. Chain transfer to these species will lead to the formation of chains which do not contain the active group.

With these considerations in mind, the polymerization process according to the present invention is typically performed under the same or similar conditions as conventional free-radical polymerization. Polymerization employing the above described CTAs is suitably carried out with temperatures during the reaction in the range −20 to 200° C., preferably in the range 40-160° C.

The process of this invention can be carried out in emulsion, solution or suspension in a batch, semi-batch, continuous, or feed mode. Otherwise conventional procedures can be used to produce narrow polydispersity polymers. For lowest polydispersity polymers, the CTA may be added before polymerization is initiated. For example, when carried out in batch mode in solution, the reactor is typically charged with CTA and monomer or medium plus monomer. To the mixture is then added the desired amount of initiator and the mixture is heated for a time which is dictated by the desired conversion and molecular weight. Polymers with broad, yet controlled, polydispersity or with multimodal molecular weight distribution can be produced by controlled addition of the CTA over the course of the polymerization process.

In the case of emulsion or suspension polymerization the medium will often be predominantly water, and conventional stabilizers, dispersants and other additives may be present. For solution polymerization, the reaction medium can be chosen from a wide range of media to suit the monomer(s) being used.

As has already been stated, the use of feed polymerization conditions allows the use of CTAs with lower transfer constants and allows the synthesis of block polymers that are not readily achieved using batch polymerization processes. If the polymerization is carried out as a feed system the reaction can be carried out as follows. The reactor is charged with the chosen medium, the CTA and, optionally, a portion of the monomer(s). Into a separate vessel is placed the remaining monomer(s). Initiator is dissolved or suspended in reaction medium in another separate vessel. The medium in the reactor is heated and stirred while the monomer+medium and initiator+medium are introduced, for example, by a syringe pump or other pumping device. The rate and duration of feed is determined largely by the quantity of solution, the desired monomer/CTA/initiator ratio and the rate of the polymerization. When the feed is complete, heating can be continued for an additional period.

Applications for polymers produced by the processes of the present invention include, for example, coatings, such as clear coats and base coat finishes or paints for automobiles and other vehicles or maintenance finishes for a wide variety of substrates. Such coatings can further include pigments, durability agents, corrosion and oxidation inhibitors, rheology control agents, metallic flakes and other additives. Block and star, and branched polymers can be used as compatibilizers, thermoplastic elastomers, dispersing agents or rheology control agents. Additional applications for these polymers are in the fields of imaging, electronics (e.g., photoresists), engineering plastics, adhesives, and sealants.

DEFINITIONS

In the context of the present invention, alkyl is intended to include linear, branched, or cyclic hydrocarbon structures and combinations thereof. Lower alkyl refers to alkyl groups of from 1 to 4 carbon atoms. Lower alkyl groups include methyl, ethyl, n-propyl, isopropyl, and n-, s- and t-butyl. Preferred alkyl groups are those of $C_{20}$ or below. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl Aryl and heteroaryl mean 5- or 6-membered monocyclic ring structures, as well as polycyclic aryl and polycyclic heteroaryl. Polycyclic aryl groups are those derived from polycyclic aromatic hydrocarbons (PAH), and particularly, fused systems (fused carbocycles) as defined by the Chemical Abstracts Index Guide, 1997 edition, that is, having at least two rings of five or more members and containing only "ortho" or "ortho- and peri-" fusions. Examples of these include, but are not limited to, naphthalene, fluorene, phenanthrene, anthracene, pyrene and perylene. Likewise, polycyclic heteroaryl groups are those derived from polycyclic heteroaromatic compounds, particularly, fused systems (fused heterocycles), containing 0-3 heteroatoms selected from nitrogen, oxygen or sulfur, such as carbazole, phenothiazine, and thianthrene. Aromatic 6- to 14-membered carbocyclic rings include, for example, benzene, naphthalene, indane, tetralin, and fluorene; and 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl means an allyl residue attached to an aryl ring. Examples are benzyl and phenethyl. Heteroarylalkyl means an alkyl residue attached to a heteroaryl ring. Examples include pyridinylmethyl and pyrimidinylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted alkyl, cycloalkyl, or heterocyclyl refer to alkyl, cycloalkyl, or heterocyclyl wherein up to three H atoms in each residue are replaced with halogen, haloalkyl, hydroxy, lower alkoxy, carboxy, carboxalkoxy, carboxamido, cyano, carbonyl, nitro, primary amino, secondary amino, alkylthio, sulfoxide, sulfone, acylamino, acyloxy, amidino, phenyl, benzyl, heteroaryl, phenoxy, benzyloxy, heteroaryloxy, or substituted phenyl, benzyl, heteroaryl, phenoxy, benzyloxy, or heteroaryloxy.

Substituted aryl or heteroaryl refers to aryl or heteroaryl wherein up to three H atoms on one or more rings is replaced with lower alkyl, substituted alkyl, substituted alkynyl, carbonyl, nitro, halogen, haloalkyl, hydroxy, alkoxy, OCH(COOH)$_2$, cyano, primary amino, secondary amino, acylamino, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

EXAMPLES

The α cyanoaryl dithiocarboxylic esters shown below were synthesized by the method of Scheme 1.

SCHEME 1

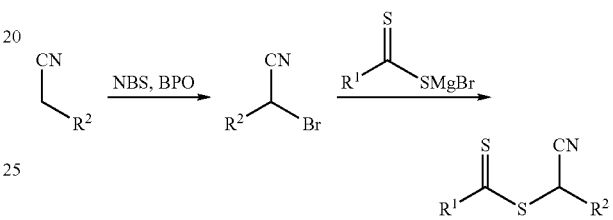

Example 1

To a 100 ml round bottom flask was added 5 ml phenyl magnesium bromide (3M solution in ethyl ether) and diluted to 20 ml with anhydrous THF. 1.2 g carbon disulfide was added dropwise to this mixture and stirred for ½ h at room temperature. Then to the dark red solution was added 3 g α-bromobenzeneacetonitrile dropwise and the mixture stirred for another 3 h. Water was added to the mixture and the organic product was extracted with diethyl ether (3×50 ml), dried with magnesium sulfate overnight and filtered. After removal of solvent and column chromatography (3:1 mixture of hexane and ethyl ether), pure α-cyanobenzyl dithiobenzoate was obtained as a red odorless solid (77% yield). Proton and carbon NMR spectra were consistent with the expected structure, CTA-CP-1.

Example 2

To a 100 ml round bottom flask was added 20 ml 2-naphthylmagnesium bromide (0.5M solution in THF). 0.76 g carbon disulfide was added dropwise to this mixture and stirred for ½ h at room temperature. Then to the dark red solution was added 2 g α-bromobenzeneacetonitrile dropwise and the mixture stirred for another 2 h. Water was added to the mixture and the organic product was extracted with diethyl ether (3×50 ml), dried with magnesium sulfate overnight and filtered. After removal of solvent and column chromatography (10:3 mixture of hexane and ethyl ether), pure α-cyanobenzyl dithionaphthalate was obtained as an orange odorless solid (63% yield). Proton and carbon NMR spectra were consistent with the expected structure, CTA-CP-2.

Example 3

To a 100 ml round bottom flask was added 20 ml p-anisylmagnesium bromide (0.49M solution in ethyl ether).

0.76 g carbon disulfide was added dropwise to this mixture and stirred for ½ h at room temperature. Then to the dark red solution was added 2 g α-bromobenzeneacetonitrile dropwise and the mixture stirred for another 2 h. Water was added to the mixture and the organic product was extracted with diethyl ether (3×50 ml), dried with magnesium sulfate overnight and filtered. After removal of solvent and column chromatography (5:1 mixture of hexane and ethyl ether), pure α-cyanobenzyl 4-methoxydithiobenzoate was obtained as an orange odorless solid (73% yield). Proton and carbon NMR spectra were consistent with the expected structure, CTA-CP-3.

Example 4

To a 100 ml round bottom flask was added 10 ml 4-fluorophenyl magnesium bromide (1.0M solution in ethyl ether) and diluted to 20 ml with anhydrous THF. 0.76 g carbon disulfide was added dropwise to this mixture and stirred for ½ h at room temperature. Then to the dark red solution was added 2 g α-bromobenzeneacetonitrile dropwise and the mixture stirred for another 2 h. Water was added to the mixture and the organic product was extracted with diethyl ether (3×50 ml), dried with magnesium sulfate overnight and filtered. After removal of solvent and column chromatography (10:3 mixture of hexane and ethyl ether), pure α-cyanobenzyl 4-fluorodithiobenzoate was obtained as a red odorless solid (62% yield). Proton and carbon NMR spectra were consistent with the expected structure, CTA-CP-4.

Example 5

To a 100 ml round bottom flask was added 10 ml 4-tolylmagiesium bromide (1.0M solution in ethyl ether) and diluted to 20 ml with anhydrous THF. 0.76 g carbon disulfide was added dropwise to this mixture and stirred for ½ h at room temperature. Then to the dark red solution was added 2 g α-bromobenzeneacetonitrile dropwise and the mixture stirred for another 2 h. Water was added to the mixture and the organic product was extracted with diethyl ether (3×50 ml), dried with magnesium sulfate overnight and filtered. After removal of solvent and column chromatography (5:2 mixture of hexane and ethyl ether), pure α-cyanobenzyl 4-methyldithiobenzoate was obtained as a red odorless solid (48% yield). Proton and carbon NMR spectra were consistent with the expected structure, CTA-CP-6.

Example 6

To a 100 ml round bottom flask was added 20 ml 4-biphenylmagnesium bromide (0.5M solution in ethyl ether). 0.76 g carbon disulfide was added dropwise to this mixture and stirred for ½ h at room temperature. Then to the dark red solution was added 2 g α-bromobenzeneacetonitrile dropwise and the mixture stirred for another 2 h. Water was added to the mixture and the organic product was extracted with diethyl ether (3×50 ml), dried with magnesium sulfate overnight and filtered. After removal of solvent and column chromatography (5:2 mixture of hexane and ethyl ether), pure α-cyanobenzyl 4-phenyldithiobenzoate was obtained as a red odorless solid (67% yield). Proton and carbon NMR spectra were consistent with the expected structure, CTA-CP-5.

Example 7

Potassium O-ethyl dithiocarbonate (0.8 g) was dissolved in 15 ml EtOH at room temperature. Then 1 g α-bromobenzeneacetonitrile was added dropwise and the mixture stirred for another 2 h. Water was added to the mixture and the organic product was extracted with diethyl ether (3×50 ml), dried with magnesium sulfate overnight and filtered. After removal of solvent and column chromatography (10:3 mixture of hexane and ethyl ether), pure α-cyanobenzyl dithiocarbonate was obtained as odorless pale yellow needle crystals(79% yield). Proton and carbon NMR spectra were consistent with the expected structure, CTA-CP-7.

Example 8

3 g triethylamine O-ethyl dithiocarbamate was dissolved in 20 ml EtOH at room temperature. Then 2 g α-bromobenzeneacetonitrile was added dropwise and the mixture stirred for another 2 h. Water was added to the mixture and the organic product was extracted with diethyl ether (3×50 ml), dried with magnesium sulfate overnight and filtered. After removal of solvent and column chromatography (10:3 mixture of hexane and ethyl ether), pure α-cyanobenzyl dithiocarbamate was obtained as an odorless pale yellow solid (85% yield). Proton and carbon NMR spectra were consistent with the expected structure, CTA-CP-8.

CHAIN TRANSFER AGENT SYNTHESIZED

CTA-CP-1

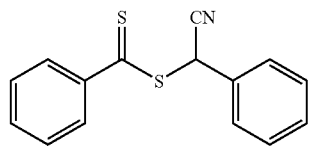

CTA-CP-2

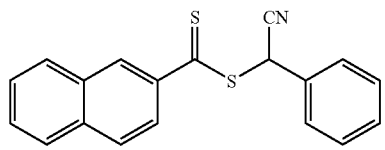

CTA-CP-3

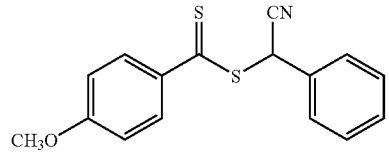

CTA-CP-4

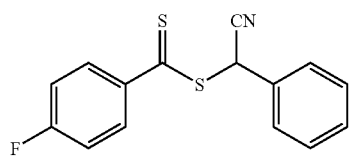

CTA-CP-5

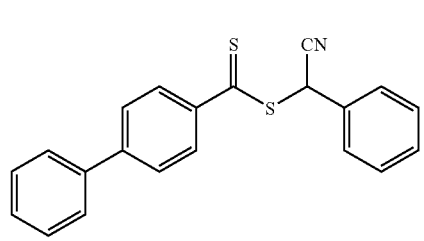

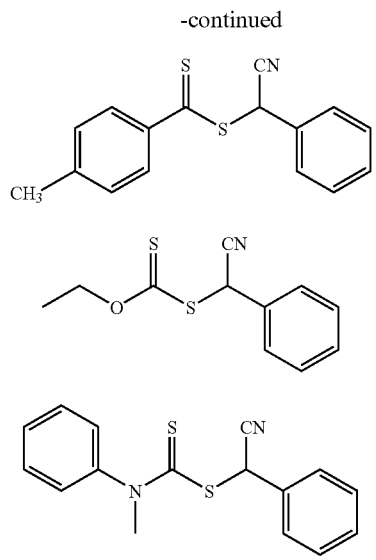

CTA-CP-6

CTA-CP-7

CTA-CP-8

Example 9

Preparation of low polydispersity poly(methyl methlacrylate) using α-cyanobenzyl dithliobenzoate A stock solution (I) of AIBN 16.5 mg in benzene (10 ml) and a stock solution (II) of α-cyanobenzyl dithiobenzoate 0.38 g in benzene (5 ml) were prepared. Aliquots of stock solution (I) (70 µl) and stock solution (II) (50 µl) were added to Schlenk tubes containing methyl methacrylate (0.7 g) and 0.3 ml benzene. The tubes were degassed by 3 consecutive freeze-pump-thaw cycles and heated at 60° C. for the times shown in Table 1 below.

TABLE 1

| Entry | Time/hr | Conv % | Mn(theo) | Mn(GPC) | PDI |
|---|---|---|---|---|---|
| 1 | 4 | 3.5 | 1750 | 3019 | 1.24 |
| 2 | 8 | 25 | 12500 | 13550 | 1.11 |
| 3 | 12 | 41 | 20500 | 24625 | 1.05 |
| 4 | 18 | 66 | 33000 | 31699 | 1.05 |
| 5 | 24 | 91 | 45500 | 45332 | 1.07 |

Excellent agreement between predicted and measured molecular weights and low polydispersities were found when the GPC was calibrated with polymethylmethacrylate standards.

Example 10

Preparation of low polydispersity polystyrene via bulk polymerization using α-cyanobenzyl dithiobenzoate Aliquots of stock solution (II) (50 µl) prepared above were added to Schlenk tubes containing styrene (0.7 g). The tubes were degassed by 3 consecutive freeze-pump-thaw cycles and heated at 110° C. for the times shown in Table 2 below.

TABLE 2

| Entry | Time/hr | Conv % | Mn(theo) | Mn(GPC) | PDI |
|---|---|---|---|---|---|
| 1 | 6 | 15.1 | 7946 | 7989 | 1.06 |
| 2 | 15 | 35.5 | 18028 | 18368 | 1.16 |
| 3 | 22 | 44 | 22280 | 23275 | 1.16 |
| 4 | 29 | 52.5 | 26775 | 27976 | 1.18 |
| 5 | 40 | 61.6 | 31058 | 31479 | 1.13 |

Excellent agreement between predicted and measured molecular weights and low polydispersities were found when the GPC was calibrated with polystyrene standards.

Example 11

Preparation of low polydispersity poly(n-butyl acrylate) using α-cyanobenzyl dithiobenzoate Aliquots of stock solution (II) (50 µl) and stock solution (I) prepared above were added to Schlenk tubes containing n-butyl acrylate (0.6 g) and 0.2 ml benzene. The tubes were degassed by 3 consecutive freeze-pump-thaw cycles and heated at 60° C. for 29 hours shown in Table 3 below.

TABLE 3

| Entry | $V_{AIBN}(\mu l)$ | Conv % | Mn(theo) | Mn(GPC) | PDI |
|---|---|---|---|---|---|
| 1 | 13 | 6.1 | 2103 | 2001 | 1.12 |
| 2 | 17 | 7.8 | 2689 | 3994 | 1.09 |
| 3 | 20 | 9.5 | 3275 | 4313 | 1.08 |
| 4 | 23 | 35.3 | 12171 | 16680 | 1.09 |
| 5 | 30 | 48.8 | 16826 | 20982 | 1.07 |

Example 12

Preparation of low polydispersity polymethylmethacrylate using α-cyanobenzyl 4-methoxydithiobenzoate A stock solution (I) of AIBN 16.5 mg in benzene (10 ml) and a stock solution (III) of α-cyanobenzyl 4-methoxy-dithiobenzoate 0.42 g in benzene (5 ml) were prepared. Aliquots of stock solution (I) (70 µl) and stock solution (III) (50 µl) were added to Schlenk tubes containing methyl methacrylate (0.7 g) and 0.3 ml benzene. The tubes were degassed by 3 consecutive freeze-pump-thaw cycles and heated at 60° C. for the times shown in Table 4 below.

TABLE 4

| Entry | Time/hr | Conv % | Mn(theo) | Mn(GPC) | PDI |
|---|---|---|---|---|---|
| 1 | 8 | 19 | 9760 | 11199 | 1.12 |
| 2 | 13 | 41 | 22384 | 23666 | 1.07 |
| 3 | 18 | 66 | 33377 | 31612 | 1.05 |

Excellent agreement between predicted and measured molecular weights and low polydispersities were found when the GPC was calibrated with polymethylmethacrylate standards.

Example 13

Preparation of low polydispersity polystyrene via bulk polymerization using α-cyanobenzyl 4-methoxydithiobenzoate A stock solution (IV) of α-cyanobenzyl 4-methoxydithiobenzoate 0.3 g in benzene (5 ml) was prepared. Aliquots of stock solution (IV) were added to Schlenk tubes containing styrene. The tubes were degassed by 3 consecutive freeze-pump-thaw cycles and heated at 110° C. for the times shown in Table 5 below.

TABLE 5

| Entry | $V_{CTA}$ (μl) | styrene/ g | Temp. | Time/ hr | Conv % | Mn (Theo) | Mn (GPC) | PDI |
| --- | --- | --- | --- | --- | --- | --- | --- | --- |
| 1 | 70 | 0.734 | 110 | 27 | 51 | 26737 | 28310 | 1.04 |
| 2 | 87 | 0.6 | 100 | 48 | 63 | 21723 | 25522 | 1.07 |

Excellent agreement between predicted and measured molecular weights and low polydispersities were found when the GPC was calibrated with polystyrene standards.

Example 14

Preparation of low polydispersity poly (n-butyl acrylate) using α-cyanobenzyl 4-methoxydithiobenzoate Aliquots of stock solution (I) (25 μl) and stock solution (IV) (87 μl) prepared in example 13 were added to a Schlenk tube containing n-butyl acrylate (0.6 g) and 0.2 ml benzene. The tube was degassed by 3 consecutive freeze-pump-thaw cycles and heated at 80° C. for 29 hours. Poly(n-butyl acrylate) was obtained (65 conv %; Mn=29193; PDI=1.06).

Example 15

Preparation of low polydispersity poly(methyl methacrylate) using α-cyanobenzyl dithionaphthalate A stock solution (I) of AIBN 16.5 mg in benzene (10 ml) was made and aliquots of stock solution (I) (50 μl) and 3.2 mg α-cyanobenzyl dithionaphthalate were added to a Schlenk tube containing methyl methacrylate (0.5 g) and 0.3 ml benzene. The tube was degassed by 3 consecutive freeze-pump-thaw cycles and heated at 60° C. for 23 h. Poly(methyl methacrylate) was obtained (conv=58%, Mn(Theo)=29000, Mn(GPC)=24558, PDI=1.04).

Example 16

Preparation of low polydispersity polystyrene via bulk polymerization using α-cyanobenzyl dithionaphthalate A stock solution (V) α-cyanobenzyl dithionaphthalate 0.328 g in benzene (5 ml) was prepared. Aliquots of stock solution (V) (87 μl) were added to a Schlenk tube containing styrene (0.6 g). The tube was degassed by 3 consecutive freeze-pump-thaw cycles and heated at 100° C. for 48 h. Polystyrene was obtained (conv=61%, Mn(Theo)=21002, Mn(GPC)=21476, PDI=1.07).

Example 17

Preparation of low polydispersity poly(n-butyl acrylate) using α-cyanobenzyl dithionaphthalate Aliquots of stock solution (I) (50 μl) and stock solution (V) (87 μl) prepared above were added to a Schlenk tube containing n-butyl acrylate (0.6 g) and 0.2 ml benzene. The tube was degassed by 3 consecutive freeze-pump-thaw cycles and heated at 80° C. for 23 h. Poly(n-butyl acrylate) was obtained (conv=42%, Mn=21728, PDI=1.06).

Example 18

Preparation of low polydispersity poly(n-butyl acrylate) using α-cyanobenzyl 4-phenyldithiobenzoate A stock solution (I) of AIBN 16.5 mg in benzene (10 ml) and a stock solution (VI) of α-cyanobenzyl 4-phenyldithiobenzoate 0.2 g in benzene (5 ml) were prepared. Aliquots of stock solution (I) (25 μl) and stock solution (VI) (153 μl) were added to a Schlenk tube containing n-butyl acrylate (0.6 g) and 0.2 ml benzene. The tube was degassed by 3 consecutive freeze-pump-thaw cycles and heated at 60° C. for 29 h. Poly(n-butyl acrylate) was obtained (conv=32%, Mn=14052, PDI=1.04).

Example 19

Preparation of low polydispersity polystyrene via bulk polymerization usizg α-cyanobenzyl 4-phenyldithiobenzoate Stock solution (VI) prepared above (153 μl) was added to a Schlenk tube containing styrene (0.6 g). The tube was degassed by 3 consecutive freeze-pump-thaw cycles and heated at 100° C. for 48 h. Polystyrene was obtained (conv=56%, Mn(Theo)=20084, Mn(GPC)=20724, PDI=1.06).

Example 20

Preparation of low polydispersity poly(n-butyl acrylate) using α-cyanobenzyl 4-fluorodithiobenzoate A stock solution (I) of AIBN 16.5 mg in benzene (10 ml) and a stock solution (VII) of α-cyanobenzyl 4-fluorodithiobenzoate 0.72 g in benzene (10 ml) were prepared. Aliquots of stock solution (I) (25 μl) and stock solution (VII) (71 μl) were added to a Schlenk tube containing n-butyl acrylate (0.6 g) and 0.2 ml benzene. The tube was degassed by 3 consecutive freeze-pump-thaw cycles and heated at 60° C. for 29 h. Poly(n-butyl acrylate) was obtained (conv=45%, Mn=24073, PDI=1.07).

Example 21

Preparation of low polydispersity polystyrene via bulk polymerization using α-cyanobenzyl 4-fluorodithiobenzoate The stock solution (VII) (71 μl) prepared above was added to a Schlenk tube containing styrene (0.6 g). The tube was degassed by 3 consecutive freeze-pump-thaw cycles and heated at 100° C. for 48 h. Polystyrene was obtained (conv=61%, Mn(Theo)=21002, Mn(GPC)=21476, PDI=1.07).

The invention claimed is:

1. A polymerization process comprising
   a. combining:
      at least one chain transfer agent of formula I,

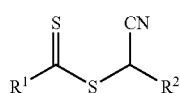

at least one monomer susceptible to free radical polymerization, and
      a free radical initiator, and;
   b. generating free radicals;
   wherein
      $R^1$ is selected from aryl, substituted aryl, alkoxy, and tertiary amino; and
      $R^2$ is aryl
   whereby a polymer, comprising repeating units derived from said at least one monomer, is formed.

2. A polymerization process according to claim 1, wherein $R^1$ is aryl.

3. A polymerization process according to claim 1, wherein $R^1$ is substituted aryl.

4. A polymerization process according to claim 1, wherein $R^1$ is alkoxy.

5. A polymerization process according to claim 1, wherein $R^1$ is tertiary amino.

6. A polymerization process according to claim 1, wherein $R^2$ is phenyl.

7. A polymerization process according to claim 1, wherein the at least one chain transfer agent is selected from the group consisting of

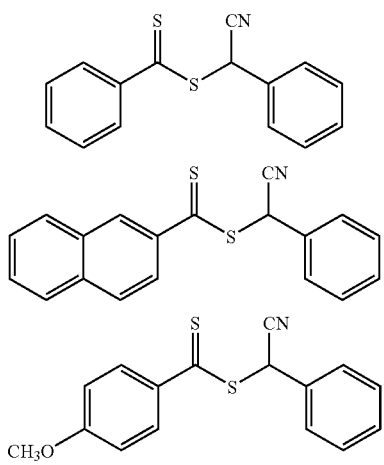

-continued

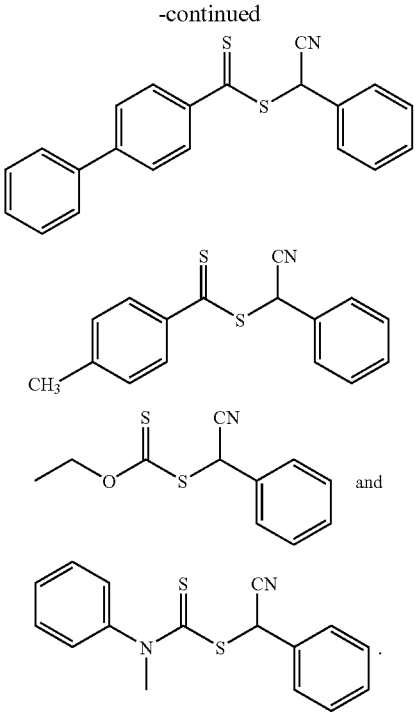

8. A polymerization process according to claim 1, wherein said at least one monomer is selected from the group consisting of vinyl monomers, acrylic and methacrylic acid, acrylate and methacrylate esters, styrene, fumarates, maleic anhydride, maleimides, and mixtures thereof.

9. A compound of formula II

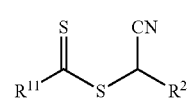

wherein
      $R^{11}$ is aryl or substituted aryl; and
      $R^2$ is aryl.

10. A compound according to claim 9, wherein $R^{11}$ is aryl.

11. A compound according to claim 9, wherein $R^{11}$ is substituted aryl.

12. A compound according to claim 9, wherein $R^{11}$ is phenyl.

13. A compound according to claim 9, wherein $R^2$ is phenyl.

14. A compound according to claim 9, selected from the group consisting of

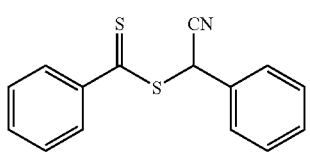

-continued
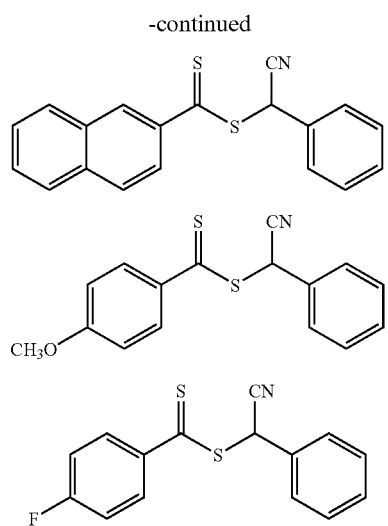
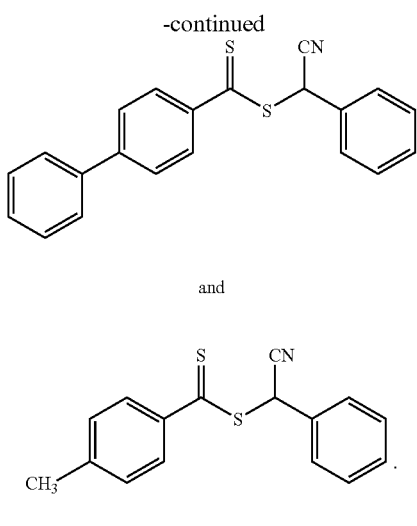
and
* * * * *